United States Patent [19]

Wheeler

[11] 4,431,650

[45] Feb. 14, 1984

[54] ESTERS OF BENZOFURANYL ACIDS

[75] Inventor: Thomas N. Wheeler, Charleston, W. Va.

[73] Assignee: Union Carbide Corporation, Danbury, Conn.

[21] Appl. No.: 219,218

[22] Filed: Dec. 22, 1980

[51] Int. Cl.$^3$ .................. A10N 43/40; C07D 405/12
[52] U.S. Cl. .................................. 424/263; 424/285; 546/269; 549/471
[58] Field of Search ................... 260/346.22; 546/269; 424/263, 285; 549/471

[56] References Cited

U.S. PATENT DOCUMENTS 4,224,330  9/1980  Henrick et al. ................. 546/274 X Primary Examiner—Richard Raymond
Attorney, Agent, or Firm—D. L. Calson; Wm. E. Dickheiser; J. A. Shedden

[57] ABSTRACT

This invention relates to novel esters of benzofuranyl acids, novel intermediates therefor, synthesis thereof, and the control of pests.

8 Claims, No Drawings

ESTERS OF BENZOFURANYL ACIDS

SUMMARY OF THE INVENTION

The esters of the present invention are represented by the following formula (A):

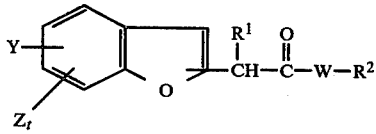
(A)

wherein,

W is oxygen; t is zero or one, each of Y and Z is, independently, selected from hydrogen, bromo, chloro, fluoro, lower alkyl, lower alkoxy, lower haloalkoxy and lower haloalkyl; $R^1$ is lower alkyl, lower alkenyl or lower cycloalkyl;

$R^2$ is selected from the groups,

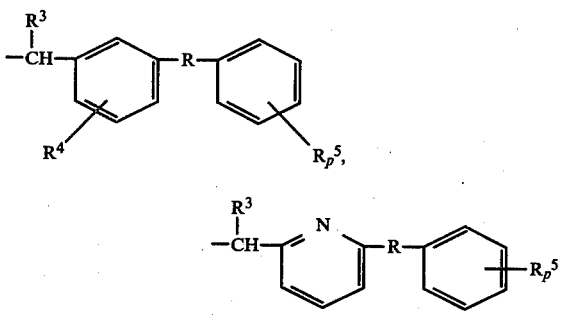

R is oxygen, sulfur, or methylene, $R^3$ is hydrogen, cyano, ethynyl, methyl, ethyl, trifluoromethyl, or dibromovinyl;

$R^4$ is hydrogen or fluoro;

$R^5$ is hydrogen, bromo, chloro, fluoro, methyl, methoxy, or trifluoromethyl; and p is zero, one or two.

The compounds of the present invention represented by formula (A) are useful agents for the control of pests such as insects and acarids.

In the description hereinafter and the appended claims, each of R through $R^5$, W, Y, Z, P and t is as defined hereinabove, unless otherwise specified.

DESCRIPTION OF THE INVENTION

The compounds of formula (A) wherein W is oxygen can be synthesized by esterification of an acid of formula (I) with an alcohol of formula II or III,

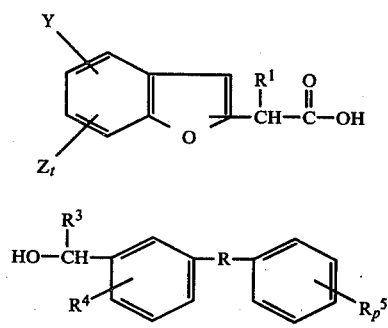

I

II

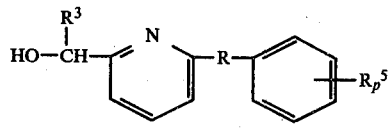

III

The esterification can be carried out by reaction of an acid of formula I, salt thereof or the acid halide with an alcohol of formula II, or III to form a carboxylic ester of formula A. For example, an acid chloride of the acid of formula I is reacted with an alcohol of formula II or III in an organic solvent such as diethyl ether, benzene, tetrahydrofuran (THF), dimethylformamide (DMF), hexamethylphosphoric-triamide (HMPA) and mixtures thereof. Alternatively, a salt such as the potassium or sodium salt of an acid of formula I is reacted with a halide such as the bromide or chloride of an alcohol of formula II or III or the mesylate or tosylate of the alcohol to form a carboxylic ester of formula A.

The benzofuran acetic acids of formula I are prepared from benzofuran by chlromethylation, conversion of the chloromethylbenzofurans to cyanomethylbenzofurans, alkylation of the cyanomethylbenzofurans and hydrolysis to the benzofuranyl acids of formula I. This method is demonstrated in detail in Example I.

The following terms, wherever used in the description herein and the appended claims, have the meaning defined below, unless otherwise specified hereinafter.

The term "lower alkyl" refers to an alkyl group, straight or branched, having a chain length of one to six carbon atoms. The term "lower haloalkyl" refers to an alkyl group substituted with one or three halogen atoms such as chloromethyl, fluoromethyl, trifluoromethyl, 2,2,2-trifluoroethyl, 6-chlorohexyl, 2-fluoroethyl, and the like. The term "lower alkoxy" refers to an alkoxy group, straight or branched, having a chain length of one to six carbon atoms. The term "lower haloalkoxy" refers to an alkoxy group substituted with such as dichloromethoxy, trifluoromethoxy, difluoromethoxy, and the like.

The term "lower alkenyl" refers to an ethylenically unsaturated hydrocarbon group, straight or branched, having a chain length of two to six carbon atoms and one ethylenic bond such as vinyl, 3-butenyl, 2-hexenyl, i-propenyl, and the like.

The compounds of the present invention of formula (A) have one or more asymmetric carbon atoms. The present invention includes each of the optical isomers and racemic mixtures thereof. In the examples hereinafter, unless otherwise specified, the compound prepared is a racemic mixture.

The compounds of the present invention of formula A are useful pest control agents, particularly for the control of insects and acarids. In the use of the compounds of formula A for combating insects and acarids for the protection of agricultural crops, for example soybeans, cotton, alfalfa, etc., a compound of formula A, or mixtures thereof, together with a carrier is applied to the locus in a pesticidally effective amount. The carrier can be liquid or solid and include adjuvants such as wetting agents, dispersing agents and other surface active agents. The compounds of formula A can be used in formulations such as wettable powders, solutions, dusts, granules, emulsifiable concentrates, and the like. Suitable solid carriers include natural and synthetic silicates and clays, carbon or charcoal granules, natural and synthetic resins, waxes, and the like. Suitable liquid carriers include water, aromatic hydrocarbons, alcohols, vegetable and mineral oils, ketones, and the like. The amount of a compound of formula A in the formulation can vary widely, generally within the range of about 0.01 percent to about 90.0 percent, by weight.

The compounds of the present invention are effective on many different insects and on acarids. The compounds are effective control agents for insects. Depending upon the particular combination of the substituents of formula A herein, the compounds have a broad or relatively narrow spectrum of unusually high pesticidal activity on insects and acarids. Among the pests against which the compounds of the present invention are pesticidally effective are insects of the order Lepidoptera, Orthoptera, Heteropters, Homoptera, Diptera, Coleoptera or Hymenoptera, and acarids of the order Acarina including mites of the family Tetranychidae or Tarsonemidae and ticks such as Ornithodoros.

The compounds of the present invention can be used in combination with other pesticides such as the carbamates, phosphates, and insect growth regulators, e.g. propoxur, carbaryl, naled, dichlorvos, methoprene, kinoprene, hydroprene, cyhexatin, resmethrin, permethrin and funvalerate.

The following examples are provided to illustrate the practice of the present invention. Temperature is given in degrees centigrade. RT means room temperature.

EXAMPLES

Example I 2-(2-benzofuranyl)-3-methyl-2-butanoic acid

Part A: Synthesis of 2-chloromethylbenzofuran

A 1 l R.B. flask was equipped with a mechanical stirrer, addition funnel, and gas inlet tube. The flask was charged with 212 ml of conc. HCl, 127 ml of benzene, and 38.14 g of paraformaldehyde, then cooled to 0° C. and saturated with hydrogen chloride gas. While maintaining the temperature at 0°–1° C. add the 50.0 g (0.423 mol) of 2,3-benzofuran in a slow dropwise fashion. When the addition was complete, the mixture was stirred 2½–3 hours at room temperature.

The mixture was diluted with ice water and the benzene layer separated. The aqueous layer was extracted once with benzene. The combined benzene layers were washed to neutrality with 10% NaHCO₃, then dried (MgSO₄), and the benzene removed on the rotary evaporator. The crude product was vacuum distilled through a vigreux column to give 21.41 g (30%) of the desired product, b.p. 82°–86° C./1.00 mm of Hg. The product was identified by N.M.R. and I.R. spectroscopy.

Part B: Synthesis of 2-benzofuranacetonitrile

A 250 ml of R.B. flask was equipped with a magnetic stirrer and a reflux condenser with nitrogen inlet. The flask was charged with 21.41 g (0.129 mol) of 2-chloromethylbenzofuran, 9.45 g (0.193 mol) of sodium cyanide, 50 ml of toluene, 8.8 ml of water, and 2.08 g of Aliquat 336. The mixture was refluxed with vigorous stirring for one hour under nitrogen. During this period, the mixture turned dark red. The reaction mixture was cooled to room temperature, and the toluene decanted from the sodium cyanide residue. This residue of salts was washed with toluene, and the combined toluene fractions were washed three times with brine, dried (MgSO₄), and the toluene removed under vacuum to yield 19.16 g of a dark red oil. This was vacuum distilled to give 11.23 g (55% yield) of the desired product, bp 96°–110°/0.25 mm, as a nearly colorless oil which solidified upon standing. The product was identified by I.R. and N.M.R. spectroscopy.

Part C: Synthesis of 2-isopropylbenzofuranacetonitrile

A 500 ml R.B. flask was equipped with a mechanical stirrer, reflux condenser with nitrogen inlet, and addition funnel. The flask was charged with 4.11 g (0.0856 mol) of 50% sodium hydride in a mineral oil dispersion. The oil was removed by two washings with toluene, then 85 ml of toluene was added followed by 11 ml of DMF and 17.54 g (0.143 mol) of 2-bromopropane. This mixture was warmed to 70° C. and the 11.23 g (0.0713 mol) of 2-benzofuranacetonitrile added, dropwise, as a solution in 25 ml of toluene. When addition was complete, the mixture was warmed to 80°–85° C. for five hours, then allowed to stir overnight at room temperature. The mixture was poured into ice water, the toluene separated, and the aqueous layer extracted with ether. The combined organic layers were washed three times with water, dried (MgSO₄), and the solvent removed to leave 14.9 g of a red oil. This was vacuum distilled to give 11.4 g (86% yield) of the desired product, bp 99°–114° C. at 0.20–0.25 mm Hg. The product was identified by I.R. and N.M.R. spectroscopy.

Part D: Synthesis of 2-(2-benzofuranyl)-3-methylbutanoic acid

A mixture of 11.44 g (0.0574 mol) of 2-isopropylbenzofuranacetonitrile, 18.94 g (0.287 mol) of potassium hydroxide, 20 ml of water, and 150 ml of ethylene glycol was heated to 140° C. for 24 hr. The cooled mixture was then poured into three volumes of water, and extracted twice with ether. The aqueous layer was cooled in ice and acidified with 6 N HCl. The resulting oil was extracted into ether, and the ether was removed under vacuum to afford 7.39 g (59% yield) of the desired product. This was not purified, but was identified by I.R. and N.M.R. spectroscopy.

Example II (α-cyano-m-phenoxybenzyl) 2-(2-benzofuranyl)-3-methylbutanoate

The acid chloride was prepared by refluxing 25 ml of carbon tetrachloride containing 3.70 g (0.0170 mol) of 2-(2-benzofuranyl)-3-methylbutanoic acid, 4.05 g (0.034 mol) of thionyl chloride, and 2 drops of pyridine for 1 hour.

The solvent was removed and the residue was taken up in 25 ml of carbon tetrachloride, cooled in an ice bath, and a solution of 5.75 g (0.0255 mol) α-cyano-m-phenoxybenzyl alcohol and 2.69 g (0.0340 mol) of pyridine added dropwise. The mixture was stirred overnight at room temperature, washed three times with 5% HCl, twice with water, dried (MgSO₄), and the solvent removed to afford 7.75 g of a yellow oil. This was purified by chromatographing through silica gel with hexane-ethyl acetate to give 2.70 g (37% yield) of the desired product.

| Analysis | C | H | N |
|---|---|---|---|
| Calc. | 76.22 | 5.45 | 3.29 |
| Found | 76.70 | 5.55 | 2.61 |

Selected species of the new compounds were evaluated to determine their pesticidal activity against mites and certain insects, including an aphid, a mite, a southern army worm (SAW), a mexcian bean bettle (MBB) and a housefly (HF).

Suspensions of the test compounds were prepared by dissolving one gram of compound in 50 milliliters of acetone in which had been dissolved 0.1 gram (10 percent of the weight of compound) of an alkylphenoxy polyethoxyethanol surfactant, as an emulsifying or dispersing agent. The resulting solution was mixed into 150 milliliters of water to give roughly 200 milliliters of a suspension containing the compound in finely divided form. The thus-prepared stock suspension contained 0.5 percent by weight of compound. The concentrations in parts per million by weight employed in the tests described hereinbelow were obtained by appropriate dilutions of the stock suspension with water. The test procedures were as follows:

Bean Aphid Foliage Spray Test

Adults and nymphal stages of the bean aphid (Aphis fabae Scop.) reared on potted dwarf nasturtium plants at 65°–70° F. and 50-70 percent relative humidity, constituted the test insects. For testing purposes, the number of aphids per pot was standardized to 100-150 by trimming plants containing excess aphids.

The test compounds were formulated by diluting the stock suspension with water to give a suspension containing 500 parts of test compound per million parts of final formulation.

The potted plants (one pot per compound tested) infested with 100-150 aphids, were placed on a revolving turntable and sprayed with 100-110 milliliters of test compound formulation by use of a DeVilbiss spray gun set at 40 psig. air pressure. This application, which lasted 25 seconds, was sufficient to wet the plants to run-off. As a control, 100-110 milliliters of a water-acetone-emulsifier solution containing no test compound were also sprayed on infested plants. After spraying, the pots were placed on their sides on a sheet of white standard mimeograph paper which had been previously ruled to facilitate counting. Temperature and humidity in the test room during the 24 hour holding period were 65°–70° F. and 50-70 percent, respectively. Aphids which fell onto the paper and were unable to remain standing after being uprighted were considered dead. Aphids remaining on the plants were observed closely for movement and those which were unable to move the length of the body upon stimulation by prodding were considered dead. Percent mortality was recorded for various concentration levels.

Southern Armyworm Leaf Spray Bait Test

Larvae of the southern armyworm (*Spodoptera eridania*, (Cram.)), reared on Tendergreen bean plants at a temperature of 80°±5° F. and a relative humidity of 50± percent, constituted the test insects.

The test compounds were formulated by diluting the stock suspension with water to give a suspension containing 500 parts of test compound per million parts of final formulation. Potted Tendergreen bean plants of standard height and age were placed on a revolving turntable and sprayed with 100-110 milliliter of test compound formulation by use of a DeVilbiss spray gun set at 10 psig air pressure. This application, which lasted 25 seconds, was sufficient to wet plants to run-off As a control, 100-110 milliliters of a water-acetone-emulsifier solution containing no test compound were also sprayed on infested plants. When dry, the paired leaves were separated and each one was placed in a 9 centimeter Petri dish lined with moistened filter paper. Five randomly selected larvae were introduced into each dish and the dishes were closed. The closed dishes were labeled and held at 80°-85° F. for three days. Although the larvae could easily consume the whole leaf within twenty-four hours, no more food was added. Larvae which were unable to move the length of the body, even upon stimulation by prodding, were considered dead. Percent mortality was recorded for various concentration levels.

Mexican Bean Beetle Leaf Spray Test

Fourth instar larvae of the Mexican bean beetle (*Epilachna variestis*, Muls.), reared on Tendergreen bean plants at a temperature of 80°±5° F. and 50±5 percent relative humidity, were the test insects.

The test compounds were formulated by diluting the stock suspension with water to give a suspension containing 500 parts of test compound per million parts of final formulation. Tendergreen bean plants of standard height and age were placed on a revolving turntable and sprayed with 100-110 milliliters of test compound formulation by use of a DeVilbiss spray gun set at 10 psig air pressure. This application, which lasted 25 seconds, was sufficient to wet plants to run-off. As a control, 100-110 milliliters of a water-acetone-emulsifier solution containing no test compound were also sprayed on infested plants. When dry, the paired leaves were separated and each was placed in a 9 centimeter Petri dish lined with moistened filter paper. Five randomly selected larvae were introduced into each dish, and the dishes were closed. The closed dishes were labeled and held at a temperature of 80°±5° F., for three days. Although the larvae could easily consume the leaf within 24 to 48 hours, no more food was added. Larvae which were unable to move the length of the body, even upon stimulation, were considered dead.

Fly Bait Test

Four to six day old adult house flies (*Musca domestica*, L.), reared according to the specifications of the Chemical Specialities Manufacturing Association (Blue Book, McNair-Dorland Co., N.Y. 1954; pages 243-244, 261) under controlled conditions of 80±°F. and 50±5 percent relative humidity, were the test insects. The flies were immobilized by anesthetizing with carbon dioxide and twenty five immobilized individuals, males and females, were transferred to a cage consisting of a standard food strainer about five inches in diameter which was inverted over a wrapping-paper-covered surface. The test compounds were formulated by diluting the stock suspension with a 10 percent (by weight) sugar solution to give a suspension containing 500 parts of test compound per million parts of final formulation, by weight. Ten milliliters of the test formulation were added to a souffle cup containing a one-inch square of an absorbent cotton pad. This bait cup was introduced and centered on the blotting paper under the food strainer prior to admitting the anesthetized flies. The caged flies were allowed to feed on the bait for twenty four hours, at a temperature of 80°±5° F. and the relative humidity of 50±5 percent. Flies which showed no sign of movement on prodding were considered dead.

Mite Foliage Spray Test

Adults and nymphal stage of the two-spotted mite (*Tetranychus urticae* Koch), reared on Tendergreen bean plants at 80±5 percent relative humidity, were the test organisms. Infested leaves from a stock culture were placed on the primary leaves of two bean plants six to eight inches in height, growing in a two-and-a-half inch clay pot. 150-200 Mites, a sufficient number for testing, transferred from the excised leaves to the fresh plants in a period of twenty four hours. Following the twenty four hour transfer period, the excised leaves were removed from the infested plants. The test compounds were formulated by diluting the stock suspension with water to give a suspension containing 500 parts of test compound per million parts of final formulation. The potted plants (one pot per compound) were placed on a revolving turntable and sprayed with 100-110 milliliters of test compound formulation by use of a DeVilbiss spray gun set at 40 psig, air pressure. This application, which lasted 25 seconds, was sufficient to wet the plants to run-off. As a control, 100-110 milliliters of a water solution containing acetone and emulsifier in the same concentrations as the test compound formulation, but containing no test compound, were also sprayed on infested plants. The sprayed plants were held at 80±5 percent relative humidity for six days, after which a mortality count of motile forms was made. Microscopic examination for motile forms was made on the leaves of the test plants. Any individual which was capable of locomotion upon prodding was considered living.

The results of these tests are set forth in Table I below. In these tests the pesticidal activity of the compounds against aphid, mite, Southern Armyworm, Bean Beetle and house fly was rated as the lethal dose (in ppm) required to kill 50% of the pest population ($LD_{50}$).

What is claimed is:

1. A compound of the following formula:

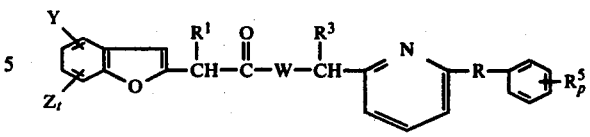

wherein:
W is oxygen;
t is zero or one;
Y and Z are independently hydrogen, bromo, chloro, fluoro, lower alkyl, lower alkoxy, lower haloalkoxy or lower haloalkyl;
$R^1$ is lower alkyl, lower alkenyl or lower cycloalkyl;
R is oxygen, sulfur, or methylene;
$R^3$ is hydrogen, cyano, ethynyl, methyl, ethyl, trifluoromethyl or dibromovinyl;
$R^5$ is hydrogen, bromo, chloro, fluoro, methyl, methoxy or trifluoromethyl; and
p is zero or one.

2. A compound according to claim 1 wherein $R^1$ is isopropyl and t is zero or one.
3. A compound according to claim 2 wherein $R^3$ is hydrogen, cyano or methyl.
4. A compound according to claim 3 wherein t is zero, Y is in the 5 or 6 position, Y is hydrogen, chlori, fluoro, methyl, methoxy or trifluoromethyl, and p is zero or one.
5. A compound according to claim 4 wherein R is oxygen and p is zero.
6. A compound according to claim 4 wherein R is oxygen and $R^5$ is chloro or fluoro in the 3 or 4 position.
7. A compound according to claim 4 wherein $R^3$ is methyl.
8. A process for the control of insects or acarids which comprises applying an insecticidally or acaricidally effective amount of a compound of claim 1, to said insects or acarids or the locus thereof.

TABLE I

| BIOLOGICAL ACTIVITY ($LD_{50}$, ppm) OF SELECTED NEW COMPOUNDS | | | | | | | | |
|---|---|---|---|---|---|---|---|---|
| | | | | | | Phytotoxicity* | | |
| Structure | Aphid | Mite | SAW | MBB | HF | Corn | Cott. | Soybean |
| (structure 1) | ~0.7 | 210 | ~45 | 11 | 23 | 1 | 1 | 1 |
| (structure 2) | 0.8 | 200 | 52 | 5 | ~180 | 1 | 1 | 1 |

*1 = No plant injury at a dose of 2500 ppm.
NR = Not Run
NA = No Activity
SAW = Southern Army Worm
MBB = Mexican Bean Beetle
HF = Housefly

UNITED STATES PATENT AND TRADEMARK OFFICE
CERTIFICATE OF CORRECTION

PATENT NO. : 4,431,650

DATED : February 14, 1984

INVENTOR(S) : Thomas N. Wheeler

It is certified that error appears in the above-identified patent and that said Letters Patent are hereby corrected as shown below:

Column 1: line 47; delete "P", insert ---p---.

Column 8: claim 4; line 2, delete "chlori", insert ---chloro---.

Signed and Sealed this

Second Day of October 1984

[SEAL]

Attest:

Attesting Officer

GERALD J. MOSSINGHOFF

*Commissioner of Patents and Trademarks*